(12) United States Patent
Wittenberger et al.

(10) Patent No.: US 9,867,660 B2
(45) Date of Patent: Jan. 16, 2018

(54) VEIN OCCLUSION ASSESSMENT USING TEMPERATURE

(71) Applicant: MEDTRONIC CRYOCATH LP, Toronto (CA)

(72) Inventors: Dan Wittenberger, L'Île-Bizard (CA); Rachid Mahrouche, Lasalle (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 409 days.

(21) Appl. No.: 13/799,714

(22) Filed: Mar. 13, 2013

(65) Prior Publication Data

US 2014/0276709 A1  Sep. 18, 2014

(51) Int. Cl.
    *A61B 18/14* (2006.01)
    *A61B 19/00* (2006.01)
    *A61B 18/02* (2006.01)
    *A61B 18/00* (2006.01)

(52) U.S. Cl.
    CPC .......... *A61B 18/1492* (2013.01); *A61B 18/02* (2013.01); *A61B 2018/0022* (2013.01); *A61B 2018/00375* (2013.01); *A61B 2018/00577* (2013.01); *A61B 2018/00797* (2013.01); *A61B 2018/00839* (2013.01); *A61B 2018/0212* (2013.01); *A61B 2018/0262* (2013.01)

(58) Field of Classification Search
    CPC ........ A61B 18/1492; A61B 2018/0022; A61B 2018/00577; A61B 2018/00797; A61B 2018/0212; A61B 18/02
    USPC ............................................ 606/21; 600/549
    See application file for complete search history.

(56) References Cited

U.S. PATENT DOCUMENTS

| 5,009,234 A * | 4/1991 | Alt .......................... A61B 5/028 600/485 |
| 6,179,824 B1 * | 1/2001 | Eggers .................... A61B 18/12 604/28 |
| 6,245,026 B1 | 6/2001 | Campbell et al. |

(Continued)

FOREIGN PATENT DOCUMENTS

| CN | 102027427 B | 10/2013 |
| EP | 1881795 B1 | 11/2010 |
| WO | 2011072186 A1 | 6/2011 |

OTHER PUBLICATIONS

International Search Report and Written Opinion dated May 27, 2014 for International Application Serial No. PCT/CA2014/000178, International Filing Date: Mar. 6, 2014 consisting of 7 pages.

(Continued)

*Primary Examiner* — Christopher D Koharski
*Assistant Examiner* — Pamela M Bays
(74) *Attorney, Agent, or Firm* — Christopher & Weisberg, P.A.

(57) ABSTRACT

A medical system, comprising an ablation catheter is disclosed. The ablation catheter includes an elongate shaft with a proximal end, a distal end and a lumen disposed between the proximal end and the distal end. The ablation catheter also includes an expandable element in fluid communication with the lumen, a first temperature sensor operable to measure a first temperature; and a second temperature sensor operable to measure a second temperature. The first temperature sensor and the second temperature sensor are longitudinally separated from each other by at least a portion of the expandable element.

9 Claims, 4 Drawing Sheets

(56) References Cited

U.S. PATENT DOCUMENTS

| | | | |
|---|---|---|---|
| 7,753,854 B2* | 7/2010 | Bowman | A61B 5/028 |
| | | | 600/505 |
| 7,951,088 B2 | 5/2011 | Korotko et al. | |
| 2002/0045893 A1* | 4/2002 | Lane | A61B 18/02 |
| | | | 606/21 |
| 2004/0034303 A1 | 2/2004 | Korotko | |
| 2007/0032783 A1* | 2/2007 | Abboud | A61B 18/02 |
| | | | 606/21 |
| 2011/0144637 A1* | 6/2011 | Pageard | A61B 5/02158 |
| | | | 606/41 |
| 2012/0029495 A1* | 2/2012 | Wittenberger | A61B 18/02 |
| | | | 606/21 |
| 2012/0089047 A1* | 4/2012 | Ryba | A61B 18/02 |
| | | | 600/554 |

OTHER PUBLICATIONS

The State Intellectual Property Office of the People's Republic of China, Jan. 13, 2017 Notice on the First Office Action, Application No. 201480014266.X, 10 pages.

* cited by examiner

VEIN OCCLUSION ASSESSMENT USING TEMPERATURE

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to relates to catheter-based methods, systems and devices for occlusion, and in particular, utilizing measurements of one or more physiological parameters to guide an ablation treatment of cardiac arrhythmias.

BACKGROUND OF THE INVENTION

Catheter based devices are employed in various medical and surgical applications because they are relatively non-invasive and allow for precise treatment of localized tissues that are otherwise inaccessible. Catheters may be easily inserted and navigated through the blood vessels and arteries, allowing non-invasive access to areas of the body with relatively little trauma. Recently, catheter-based systems have been developed for implementation in tissue ablation for treatment of cardiac arrhythmias such as atrial fibrillation, supra ventricular tachycardia, atrial tachycardia, ventricular tachycardia, ventricular fibrillation, and the like. One such implementation involves the use of fluids with low operating temperatures, or cryogens, to selectively freeze, or "cold-treat", targeted tissues within the body.

The cryogenic treatment involves cooling a portion of the catheter to a very low temperature through the use of the cryogenic fluid flowing through the catheter. A cryogenic device uses the energy transfer derived from thermodynamic changes occurring in the flow of a cryogen therethrough to create a net transfer of heat flow from the target tissue to the device, through conductive and convective heat transfer between the cryogen and target tissue.

Structurally, cooling can be achieved through injection of high-pressure coolant into a lumen of the catheter. Upon injection, the refrigerant undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to the desired temperature.

Once refrigerant is injected into the lumen, it may be expanded inside of an expandable element (chamber), which may be positioned proximal to the target tissue. In embodiments, the expandable element may also be thermally conductive. Devices with an expandable element, such as a balloon, may be employed. In such devices, refrigerant is supplied through a catheter lumen into an expandable balloon coupled to such catheter, wherein the refrigerant acts to both: (i) expand the balloon near the target tissue for the purpose of positioning the balloon, and (ii) cool the target tissue proximal to the balloon to cold-treat adjacent tissue.

The expandable element may also serve a second function; blocking the flow of blood through the desired treatment site (occlusion). The catheter is typically of a relatively small diameter and long body, generally determined, by the diameter and length of the vascular pathways leading to the ablation site. The coolant in the catheter is highly susceptible to conductive warming effects due to the relative proximity of the catheter (and coolant) to the body tissue and blood. Furthermore, the rate of cooling is limited by the ability to circulate a sufficient mass flow of coolant through the catheter. Yet there is a requirement that the coolant itself be at a sufficiently low temperature, in some cases below freezing, at the location of the ablation. In addition, while this may be generally true, the occlusion may help reduce the heat-load at the target ablation site and not on the whole catheter.

Blocking the flow of blood using the expandable element allows more effective cooling which facilitates the treatment process and may reduce the treatment period. Effective contact to achieve occlusion may require moving, positioning, anchoring and other mechanisms for locating and stabilizing the conformation of the expandable element of the catheter. Moreover, slight changes in orientation may greatly alter the characteristics of the catheter, so that even when the changes are predictable or measurable, it may become necessary to provide positioning mechanisms of high stability or accuracy to assure adequate treatment at the designated sites. Furthermore, one must assure that the ablation is effective at the target tissue.

Known techniques for visualizing the contact between the expandable element and the target tissue include the use of radiographically opaque contrast medium to enable radiographic-mapping of the target tissue during application and operation of the catheter. Such an imaging technique may not be desirable due to the use of contrast medium and its interaction with the patient tissue. Additionally, it may be desirable to eliminate or minimize the exposure of both patient and clinician to the radiographic-mapping waves used for imaging.

It is desirable therefore, to provide improved catheter systems that are capable of providing an indication of occlusion while eliminating or significantly reducing exposure of the patient and clinician to imaging waves.

SUMMARY OF THE INVENTION

The present invention advantageously provides a method and system for determining occlusion in a blood vessel. In accordance with one embodiment, a medical system comprising an ablation catheter is disclosed. The ablation catheter includes an elongate shaft with a proximal end, a distal end and a lumen disposed between the proximal end and the distal end. The ablation catheter also includes an expandable element in fluid communication with the lumen, a first temperature sensor operable to measure a first temperature, and a second temperature sensor operable to measure a second temperature. The first temperature sensor and the second temperature sensor are longitudinally separated from each other by at least a portion of the expandable element.

In accordance with another embodiment, a method of assessing vein occlusion with an ablation catheter is disclosed. The ablation catheter includes an elongate shaft with a proximal end, a distal end and a lumen disposed between the proximal end and the distal end. The ablation catheter also includes an expandable element in fluid communication with the lumen. The method includes measuring a first temperature using a first temperature sensor, and measuring a second temperature using a second temperature sensor. The first temperature sensor and the second temperature sensor are longitudinally separated from each other by at least a portion of the expandable element.

In accordance with yet another embodiment, a medical system is disclosed. The medical system includes an ablation catheter and a control unit. The ablation catheter includes an elongate shaft with a proximal end, a distal end, a lumen disposed between the proximal end and the distal end, and an expandable element in fluid communication with the lumen. The ablation catheter also includes a first temperature sensor operable to measure a first temperature, and a second temperature sensor operable to measure a second temperature. The first temperature sensor and the second temperature sensor are longitudinally separated from each other by at least a portion of the expandable element. The control unit is operable to deliver a continuous flow of inflation fluid to the expandable element, and determine an extent of occlusion in a blood vessel when the expandable element is inserted within the blood vessel and inflated. The determination is being based at least in part on a temperature differential between the first temperature and the second temperature.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
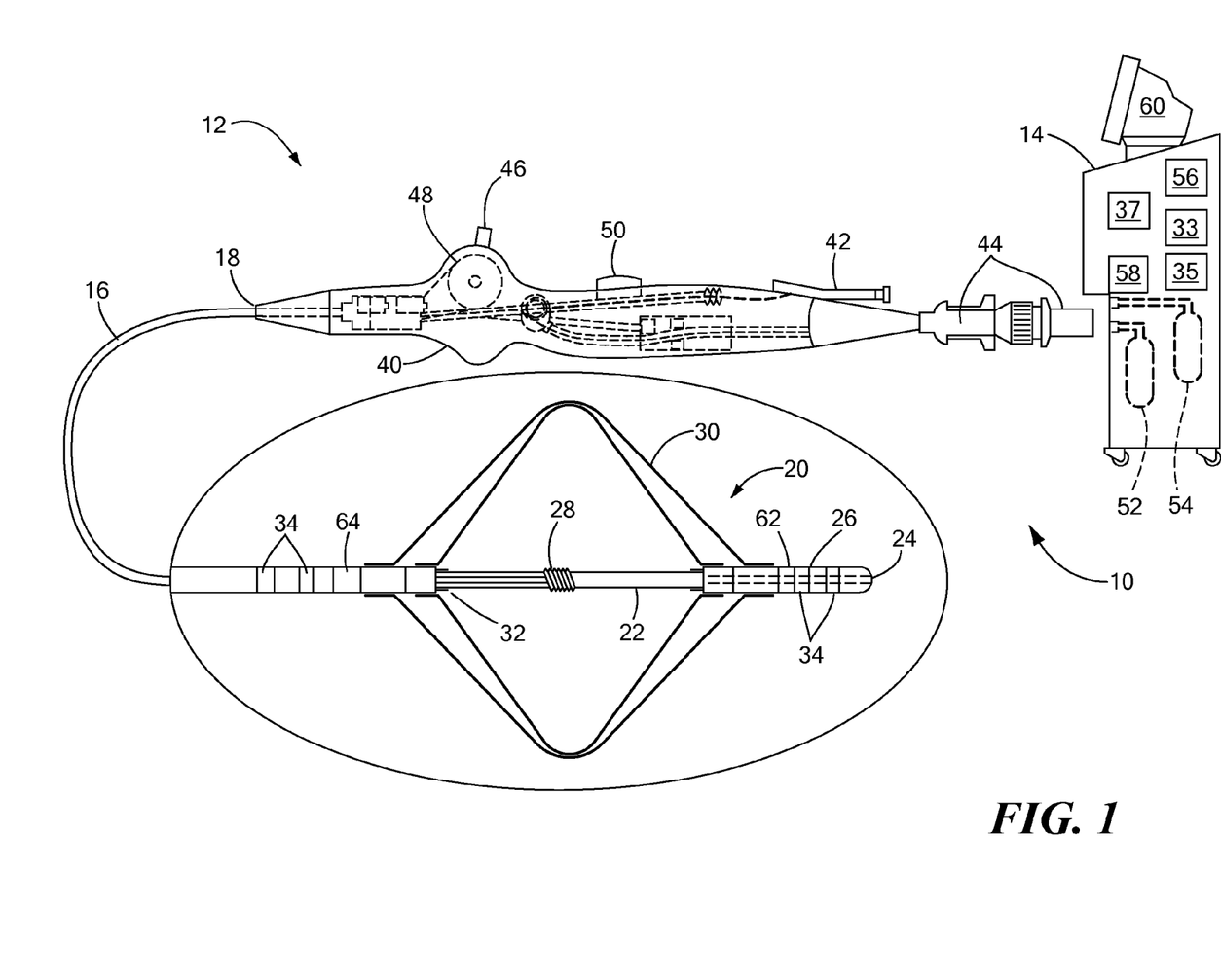
FIG. 1 is an illustration of an example of a medical system constructed in accordance with the principles of the present invention.

Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site or region. The diagnostic or treatment region(s) may deliver, for example, cryogenic therapy, radiofrequency energy, or other energetic transfer with a tissue area in proximity to the treatment region(s), including cardiac tissue.

The medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include an elongate shaft 22 at least partially disposed within a portion of the elongate body 16. The elongate shaft 22 may extend or otherwise protrude from a distal end of the elongate body 16, and may be movable with respect to the elongate body 16 in longitudinal and rotational directions. That is, the elongate shaft 22 may be slidably and/or rotatably moveable with respect to the elongate body 16. The elongate shaft 22 may further define a lumen 24 therein for the introduction and passage of a guide wire. The elongate shaft 22 has a proximal end, a distal end and a lumen 24 disposed between the proximal end and the distal end. The elongate shaft 22 may include or otherwise be coupled to a distal tip 26 that defines an opening and passage there through for the guide wire.

The medical device 12 may further include a fluid delivery conduit 28 traversing at least a portion of the elongate body and towards the distal portion. The delivery conduit 28 may be coupled to or otherwise extend from the distal portion of the elongate body 16, and may further be coupled to the elongate shaft 22 and/or distal tip of the medical device 12. The fluid delivery conduit 28 may define a lumen therein for the passage or delivery of a fluid from the proximal portion of the elongate body 16 and/or the control unit 14 to the distal portion and/or treatment region of the medical device 12. The fluid delivery conduit 28 may further include one or more apertures or openings therein, to provide for the dispersion or directed ejection of fluid from the lumen to an environment exterior to the fluid delivery conduit 28.

The medical device 12 may further include one or more expandable elements 30 at the distal portion of the elongate body 16. The expandable element 30 may be coupled to a portion of the elongate body 16 and also coupled to a portion of the elongate shaft 22 and/or distal tip 26 to contain a portion of the fluid delivery conduit 28 therein. The expandable element 30 defines an interior chamber or region that contains coolant or fluid dispersed from the fluid delivery conduit 28, and may be in fluid communication with an exhaust lumen 32 defined by or included in the elongate body 16 for the removal of dispersed coolant from the interior of the expandable element 30. The expandable element 30 may further include one or more material layers providing for puncture resistance, radiopacity, or the like.

A first temperature sensor 62 is coupled to medical device 12 at a location that may be anterior or distal to the expandable element 30. A second temperature sensor 64 may be coupled to medical device 12 at a location that may be posterior or proximal to the expandable element 30, i.e., the first temperature sensor 62 is positioned distal to the expandable element, and the second temperature sensor is positioned proximal to the expandable element. The first temperature sensor 62 and the second temperature sensor 64 may be longitudinally separated from each other by at least a portion of expandable element 30. The first temperature sensor 62 and the second temperature sensor 64 may be located anywhere on the medical device 12.

The medical device 12 may further include one or more electrically-conductive segments or electrodes 34 positioned on or about the elongate body for conveying an electrical signal, current, or voltage to a designated tissue region and/or for measuring, recording, or otherwise assessing one or more electrical properties or characteristics of surrounding tissue. The electrodes 34 may be configured in a myriad of different geometric configurations or controllably deployable shapes, and may also vary in number to suit a particular application, targeted tissue structure or physiological feature. For example, as shown in FIG. 1, the electrodes 34 may include a first pair proximate to the expandable element and a second electrode pair distal to the expandable element. The electrodes 34 may be positioned on the medical device 12 substantially equidistant from an adjacent electrode 34 in the array or may be variable distances from each adjacent electrode 34.

Each electrode 34 may be electrically coupled to an output portion of a radiofrequency signal generator, and each electrode 34 may also include a sensor, such as a thermocouple, an electrical conductivity sensor, a spectrometer, a pressure sensor, a fluid flow sensor, a pH sensor, and/or a thermal sensor (not shown) coupled to or in communication with the electrodes. The sensors may also be in communication with a feedback portion of the control unit 14 to trigger or actuate changes in operation when predetermined sequences, properties, or measurements are attained or exceeded.

Referring again to FIG. 1, the medical device 12 may include a handle 40 coupled to the proximal portion of the elongate body 16. The handle 40 can include circuitry for identification and/or use in controlling of the medical device 12 or another component of the system. Additionally, the handle 40 may be provided with a fitting 42 for receiving a guide wire that may be passed into the guide wire lumen 24. The handle 40 may also include connectors 44 that are mateable to the control unit 14 to establish communication between the medical device 12 and one or more components or portions of the control unit 14.

The handle 40 may also include one or more actuation or control features that allow a user to control, deflect, steer, or otherwise manipulate a distal portion of the medical device 12 from the proximal portion of the medical device 12. For example, the handle 40 may include one or more components such as a lever or knob 46 for manipulating the elongate body 16 and/or additional components of the medical device 12. For example, a pull wire 48 with a proximal end and a distal end may have its distal end anchored to the elongate body 16 at or near the distal portion 20. The proximal end of the pull wire 48 may be anchored to an element such as a cam in communication with and responsive to the lever 46. The medical device 12 may include an actuator element 50 that is movably coupled to the proximal portion of the elongate body 16 and/or the handle 40 for the manipulation and movement of a portion of the medical device 12, such as the shaft 22, and/or one or more portions of the electrode assemblies described above, for example.

The system 10 may include one or more treatment sources coupled to the medical device for use in an operative procedure, such as tissue ablation, for example. The control unit 14 may include a fluid supply 52 including a coolant, cryogenic refrigerant, or the like, an exhaust or scavenging system (not shown) for recovering or venting expended fluid for re-use or disposal, as well as various control mechanisms. In addition to providing an exhaust function for the fluid or coolant supply 52, the control unit 14 may also include pumps, valves, controllers or the like to recover and/or re-circulate fluid delivered to the handle 40, the elongate body 16, and/or the fluid pathways of the medical device 12. A vacuum pump 54 in the control unit 14 may create a low-pressure environment in one or more conduits within the medical device 12 so that fluid is drawn into the conduit(s)/lumen(s) of the elongate body 16, away from the distal portion 20 and towards the proximal portion 18 of the elongate body 16. One or more valves may be included, for example, one may be a low pressure proportional valve and one may be a high pressure proportional valve. Both valves may be controlled by a PID controller.

The control 14 unit may include a radiofrequency generator or power source 56 as a treatment or diagnostic mechanism in communication with the electrodes 34 of the medical device 12. The radiofrequency generator 56 may have a plurality of output channels, with each channel coupled to an individual electrode 34. The radiofrequency generator 56 may be operable in one or more modes of operation, including for example: (i) bipolar energy delivery between at least two electrodes on the medical device within a patient's body, (ii) monopolar or unipolar energy delivery to one or more of the electrodes 34 on the medical device 12 within a patient's body and through a patient return or ground electrode (not shown) spaced apart from the electrodes 34 of the medical device 14, such as on a patient's skin for example, and (iii) a combination of the monopolar and bipolar modes.

The system 10 may further include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

The control unit 14 may include one or more processors 37 and/or software modules containing instructions or algorithms to provide for the automated operation and performance of the features, sequences, calculations, or procedures described herein. For example, the control unit 14 may include a signal processing unit 58 to measure one or more electrical characteristics between the electrodes 34 of the medical device 12. Signal processing unit 58 may comprise a digital signal processor. An excitation current may be applied between one or more of the electrodes 34 on the medical device 12 and/or a patient return electrode, and the resulting voltage, impedance, or other electrical properties of the target tissue region may be measured, for example, in an electrogram. Unipolar electrograms ("EGMs") may be recorded with the mapping electrode 34 as the positive electrode, and another electrode 34 on the body surface or remote from the field or cardiac excitation as the negative electrode. The control unit 14 may further include a display 60 to display the various recorded signals and measurement, for example, an electrogram.

Processor 37 may be in communication, e.g., electrically coupled, to first temperature sensor 62 and second temperature sensor 64 to monitor the temperatures sensed by the first temperature sensor 62 and second temperature sensor 64. Control unit 14 may include a receiver 33 for receiving input signals from, for example, the first temperature sensor 62 and the second temperature sensor 64, and a transmitter 35 for transmitting signals to, for example, the first temperature sensor 62 and the second temperature sensor 64. The first temperature signal from the first temperature sensor 62 and the second temperature signal from the second temperature sensor 64 may be analyzed by the signal processing unit 58. The processor 37 and/or the signal processing unit 58 may convert signals to digital form, process those digital signals, and derive an indication of the differential temperature between the first temperature measured at first temperature sensor 62 and the second temperature measured at second temperature sensor 64. Processor 37 may derive a temperature differential between the first temperature sensor 62 and the second temperature sensor 64 based at least in part on the analysis of the first temperature signal and the second temperature signal.

Figure 2:
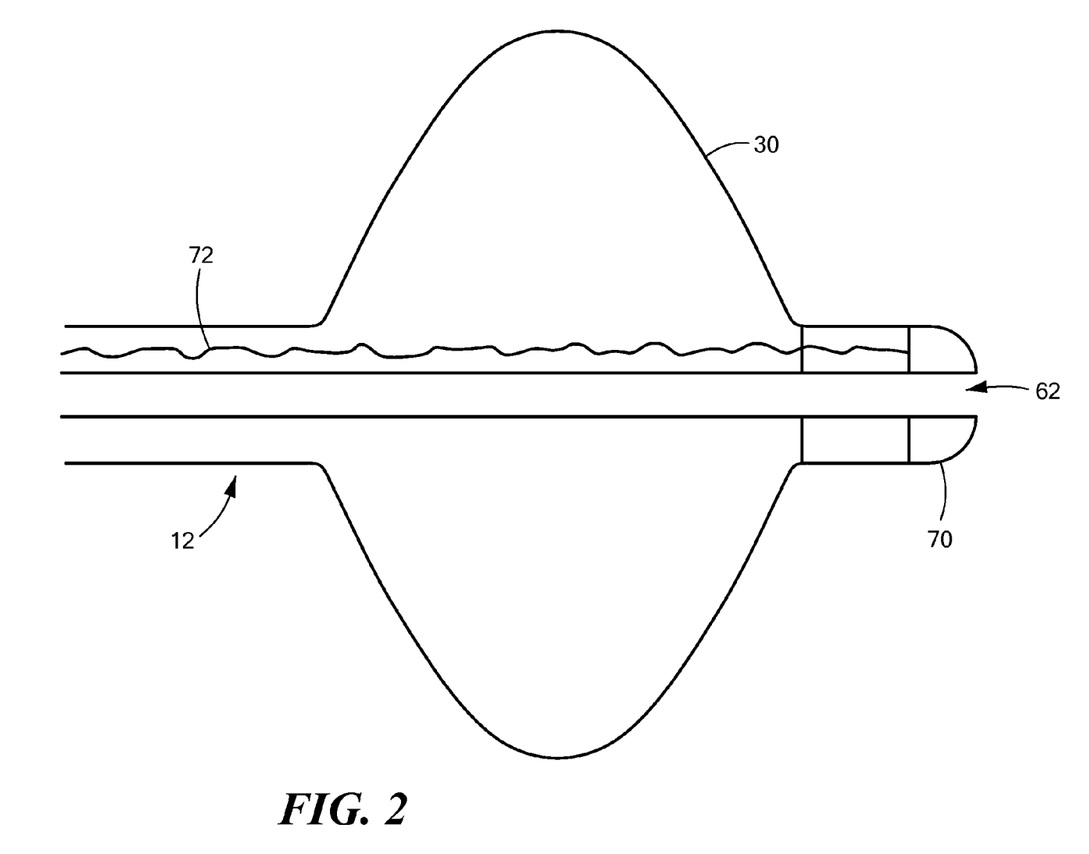
FIG. 2 is an illustration of an example of a medical device assembly constructed in accordance with the principles of the present invention.

FIG. 2 shows an exemplary temperature sensor, such as the first temperature sensor 62. The first temperature sensor 62 may include a conductive element 70 that is coupled to an electrically conductive wire 72 for electrical coupling of the conductive element 70 to electronic circuitry in control unit 14, such as processor 37. The electronic circuitry cooperates with the first temperature sensor 62 to sense the temperature of the tissue/environment surrounding the first temperature sensor 62. The temperature measurements may be used to provide information regarding occlusion. The control unit 14 may be operable to determine a temperature difference between the first temperature measured at first temperature sensor 62, and the second temperature measured at second temperature sensor 64, the temperature difference indicating the extent of occlusion in the blood vessel. The temperature sensor of FIG. 2 may be used to implement second temperature sensor 64.

Figure 3:
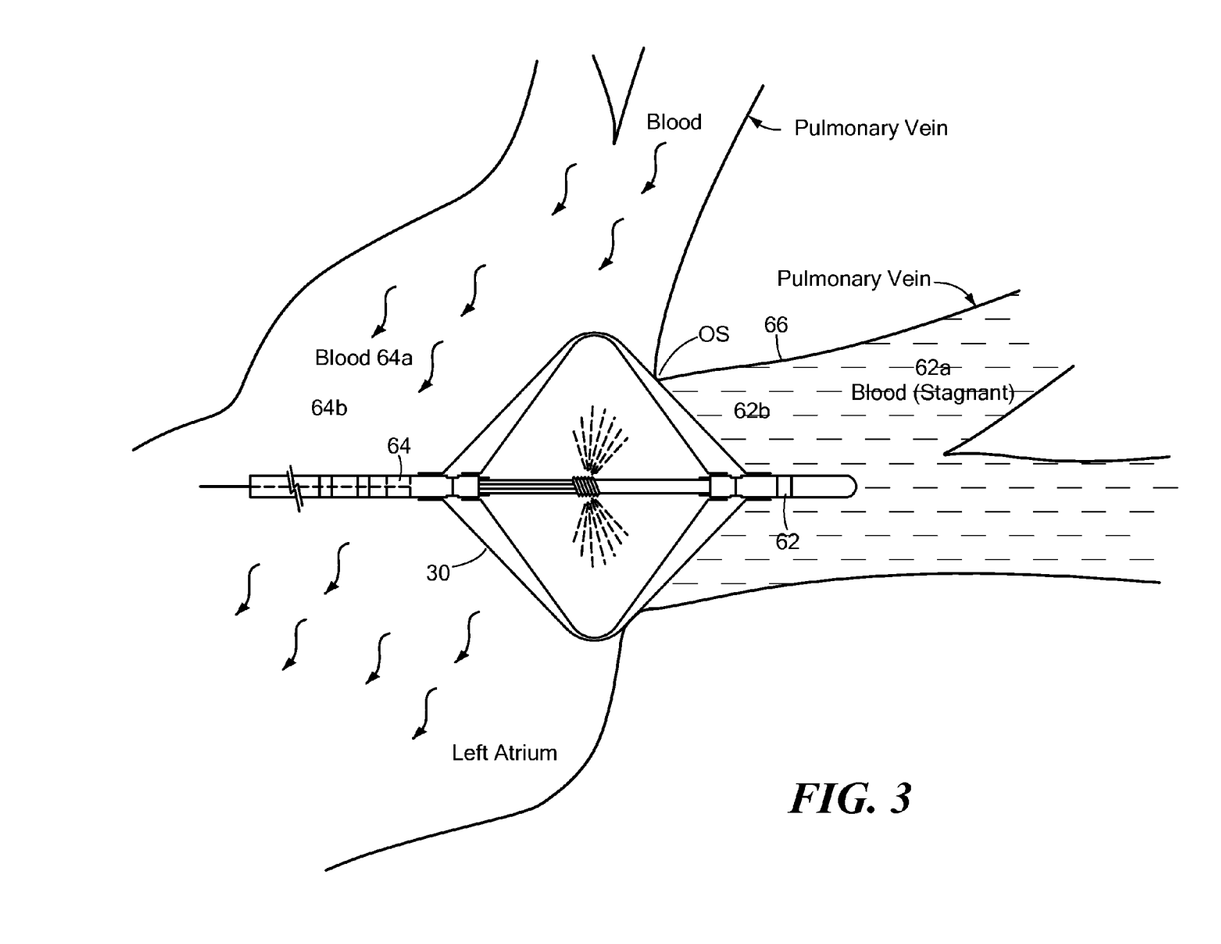
FIG. 3 is another illustration of an example of a medical device achieving full occlusion constructed in accordance with the principles of the present invention.

FIG. 3 includes the medical device 12, e.g., catheter 12, which operates to treat vascular tissue of a patient that is adjacent to the expandable element 30. To achieve this, catheter body 16 may be navigated through the vascular system to the desired vascular tissue such as a vessel 66. Examples of vessel 66 may include a left pulmonary vein, a right pulmonary vein, ostia, or other blood vessel. During deployment of the catheter 12, expandable element 30 may be deflated for ease of steering and passage through the vascular system.

Once catheter 12 is adjacent the desired site in vessel 66, expandable element 30 may be inflated. Generally, inflation of expandable element 30 will result in radial expansion of expandable element 30 to a diameter that is at least as large as that of vessel 66. The expanded expandable element 30 may then be advanced to the opening of vessel 66 to achieve contact between expandable element 30 and the opening to the interior of vessel 66. When the expandable element 30 is properly situated, the blood flow within the vessel 66 will be occluded.

The occlusion is predicated upon proper positioning of the expandable element 30 to abut with the opening of vessel 66. As previously discussed, proper positioning presents several challenges to the user. These challenges include the difficulty of navigating catheter 12 within the vascular system and the size and nature of the vascular system. Embodiments of the present disclosure utilize one or more temperature sensors, such as first temperature sensor 62 and second temperature sensor 64, to ascertain the extent of occlusion (and consequently proper location) of the expandable element 30.

In use, first temperature sensor 62 is in fluid communication with vessel 66 and measures the temperature of the blood 62a within vessel 66. When there is complete occlusion, blood 62a becomes stagnant. Second temperature sensor 64 is in fluid communication with vessel 66 and measures the temperature of the blood 64a flowing within vessel 66. Even when there is complete occlusion, blood 64a keeps flowing.

The first temperature sensor 62 operably measures the temperature of blood 62a within a body region 62b that is in fluid communication with vessel 66. The second temperature sensor 64 operably measures the temperature of blood 64a within a body region 64b that is in fluid communication with vessel 66. In an embodiment, the region 62b is an atrial chamber adjacent the vessel 66. In another embodiment, region 62b may simply be a location that is more distal within vessel 66. Accordingly, a computation of the differential temperature in region 62b and region 64b can be computed based on the temperature measurements of the first temperature sensor 62 and the second temperature sensor 64.

The expandable element 30 is shown positioned within vessel 66 in accordance with principles of the present disclosure. Catheter 12 is navigated through the vascular system and with the aid of the measured differential temperature measurements, expandable element 30 may be positioned such that its external circumferential surface is in an uninterrupted contact with the opening to the interior of vessel 66. The continuous circumferential contact between the opening of vessel 66 and expandable element 30 enables complete occlusion of blood flow 62a within vessel 66.

First temperature sensor 62 may be used in conjunction with second temperature sensor 64 to obtain the differential temperature across expandable element 30; i.e., the difference between the temperature in the region that is distal to expandable element 30 (region 62b) and the temperature in the region that is proximal to expandable element 30 (region 64b). The first temperature at first temperature sensor 62 and the second temperature at second temperature sensor 64 may be received by receiver 33 and processed by processor 37 and/or signal processing unit 58 of control unit 14.

The temperature differential between the first temperature sensor 62, e.g., the distal thermocouple, and the second temperature sensor 64, e.g., the proximal thermocouple, is measured during inflation, prior to initiating ablation (freezing). Since inflation is performed with a cool fluid which has a temperature below the body temperature of 37° Celsius, there is an initial difference between the first temperature measured at first temperature sensor 62 and the second temperature measured at second temperature sensor 64.

A continuous supply of blood 64a at a temperature of 37° Celsius washes the proximal surface of expandable element 30, e.g., the balloon, and second temperature sensor 64. As such, the temperature of the inflation fluid increases due to the heat from the blood 64a transferring to the inflation fluid, and the second temperature measured at second temperature sensor 64 increases to approximately 37° Celsius.

At approximately the same time, as long as the vein, e.g., vessel 66, is still not occluded, a continuous flow of blood 62a having a temperature of 37° Celsius washes the distal surface of expandable element 30 and first temperature sensor 62. This causes the temperature of the first temperature sensor 62 to increase and remain constant at 37° Celsius.

As full occlusion is achieved, there is no more new blood having a 37° Celsius temperature flowing toward region 62b. The first temperature measured at first temperature sensor 62 will become lower (colder) than the second temperature measured at second temperature sensor 64, as the blood 62a will become stagnant and will cool due to contact with the expandable element 30, which is being cooled by the inflation fluid, e.g., the refrigerant.

Since the heat capacity of the inflation fluid inside expandable element 30 is low and the inflation volume is also low (approximately 20 cc of refrigerant), the temperature difference between the first temperature measured at first temperature sensor 62 and the second temperature measured at second temperature sensor 64 is initially relatively small. Also, the longer it takes a physician to get occlusion, the smaller the difference between the first temperature measured at first temperature sensor 62 and the second temperature measured at second temperature sensor 64 will become. Therefore, it is difficult to ascertain whether full occlusion has been achieved, as the first temperature measured at first temperature sensor 62 and the second temperature measured at second temperature sensor 64 are almost identical.

In addition, this difference in temperature lasts a short period of time, especially when a bolus injection of refrigerant is used (as no additional refrigerant is being released into expandable element 30). The initial refrigerant may reach a temperature of 37° Celsius fairly quickly, making the difference between the first temperature measured at the first temperature sensor 62 and the second temperature measured at the second temperature sensor 64 very small. The small difference in temperatures makes it difficult to ascertain whether full occlusion has been achieved, as the effect of cooling is lost in fractions of a second when using a bolus injection of refrigerant.

Therefore, the use a continuous flow of inflation fluid is proposed. By using a continuous flow of inflation fluid, the temperature differential between the first temperature measured at the first temperature sensor 62 and the second temperature measured at the second temperature sensor 64 is maintained. Maintaining the temperature differential may make occlusion assessment easier. Specifically, when there is complete occlusion, the first temperature at first temperature sensor 62 will be a couple of degrees Celsius lower than the second temperature at second temperature sensor 64. The blood 62a becomes stagnant and becomes colder as it is in contact with the continuous flow of inflation fluid. No more warm blood flows on region 62b, i.e., blood 62a is stagnant, which causes the first temperature of first temperature sensor 62 to drop. On the other hand, the second temperature at second temperature sensor 64 is higher than the first temperature at first temperature sensor 62, as second temperature sensor 64 is in contact with flowing blood 64a having a temperature of 37° Celsius. This difference in temperature between the first temperature and the second temperature indicate full occlusion.

Control unit 14 may be configured to provide a continuous flow of inflation fluid from fluid supply 52 to the expandable element 30. The inflation fluid may be precooled prior to injection to a temperature in a range of approximately five degrees Celsius to ten degrees Celsius. Processor 37 may control the flow and amount of the continuous inflation fluid delivered to catheter 12. Processor 37 may be configured to provide a continuous flow of inflation fluid until a temperature differential that makes the determination of occlusion possible is achieved.

When the continuous flow of inflation fluid is delivered to inflate the expandable element, the continuous flow of inflation fluid may be injected at approximately 1,000 to 3,000 standard cubic centimeters per minute. Once it is determined that the extent of occlusion in the blood vessel 66 is one of a complete occlusion, processor 37 may generate a signal to increase the continuous flow of inflation fluid from fluid supply 52, so that ablation may be performed. For example, when the continuous flow of inflation is delivered to ablate at least a part of the blood vessel 66, the continuous flow of inflation fluid is injected at approximately 6,200 to 7,200 standard cubic centimeters per minute. Two proportional valves with PIDs may be driving the system 10 to have the continuous flow capability. For example, a high pressure proportional valve and a low pressure proportional valve may be used. A PID controller may regulate the injection pressure, regulating the flow and the tip temperature. Of note, although exemplary values have been provided for the amount of inflation fluid injected in standard cubic centimeters per minute, the invention is not limited to such. The inflation fluid may be injected at any value of standard cubic centimeters per minute, for example, the injection fluid may be injected at 9,000 standard cubic centimeters per minute. The volume or mass flow rate may vary depending on different factors, such as the catheter being used, the treatment to be applied, etc.

The control unit 14 may determine an extent of occlusion in a blood vessel when the expandable element 30 is inserted within the blood vessel 66 and inflated, the determining being based at least in part on a relationship of the first temperature measured at first temperature sensor 62 and the second temperature measured at second temperature sensor 64. A rate or volume of fluid flowing through the medical device 12 may further be controlled using control unit 14. For example, the volume of fluid sent to expandable element 30 may be sufficiently dimensioned or sized to completely inflate expandable element 30.

For example, using in-vivo or in-vitro modeling, appropriate temperature profiles as measured by the first temperature sensor 62 and the second temperature sensor 64 can be obtained for the case of occlusion, partial occlusion or no occlusion. These profiles can be incorporated into the control unit 14 and compared with real-time measurements to determine occlusion. Processor 37 may determine whether the extent of occlusion in the blood vessel 66 is one of complete occlusion, partial occlusion and no occlusion.

In an exemplary embodiment, a large temperature difference, e.g., greater than two degrees Celsius, between the first temperature measured by the first temperature sensor 62, and the second temperature measured by the second temperature sensor 64, may be associated with complete occlusion whereas a temperature difference less than one degree Celsius may be associated with no occlusion. Temperature differences of above one degree Celsius and below two degree Celsius may be designated as corresponding to partial occlusion. However, one skilled in the art will appreciate that the temperature variances noted above are merely illustrative.

In another exemplary embodiment, processor 37 and/or signal processing unit 58 derive an indication of the differential temperature of the blood 62a in region 62b and blood 64a in region 64b, i.e., the first temperature at the first temperature sensor 62 and the second temperature at the second temperature sensor 64. To determine the temperature differential, processor 37 may subtract the second temperature from the first temperature. The result is the temperature differential. The temperature differential may be compared against a predetermined value, predetermined values or ranges of values. Processor 37 may compare the determined temperature difference to a predetermined value of a plurality of predetermined values, wherein each predetermined value indicates an extent of occlusion in the blood vessel. The extent of occlusion may be determined based at least in part on the comparison.

Similar to the previous example, a predetermined occlusion value may be two degrees Celsius, e.g., when the temperature differential is equal to or more than two degrees Celsius, then processor 37 determines that there is full occlusion. Predetermined partial occlusion values may be values that are less than two degrees Celsius but more than or equal to one degree Celsius. When the temperature differential is less than one degree Celsius, processor 37 may determine that there is no occlusion.

The signal processor in control unit 14 may correlate the differential temperature computation with a predetermined value. When complete mechanical occlusion has been achieved, the first temperature signal measured at first temperature sensor 62 may be continuously measured and compared against the second temperature signal measured at second temperature 64. The predetermined value may be obtained by subtracting the first temperature signal from region 62b from the second temperature signal from region 64b. Computations of the differential temperature measured at region 62b and region 62b may be continuously performed and compared against the predetermined value.

The results of differential temperature computation may be delivered to a user via display 60. Additionally or alternatively, the raw waveform signals sensed by first temperature sensor 62 and second temperature sensor 64 may be received control unit 14 and displayed in raw signal waveform on display 60.

In an embodiment, control unit 14 may provide an indication to a user, such as a clinician of whether or not occlusion has been achieved or if changes have arisen based on the sensed signals. For example, control unit 14 may include a tactile alarm that may be worn by the physician to provide a vibratory signal to the physician when the signals indicate changes in the level of occlusion. Control unit 14 may also activate an audible alarm in response to occlusion changes to alert the clinician to indications of possible changes that may require readjustment of the position of catheter 12 or even termination of the process. In other embodiments, light indicators can be used to instruct the physician about the level of occlusion: for example, a green light indicating complete occlusion, an orange light indicating partial occlusion and a red light indicating no occlusion.

Figure 4:
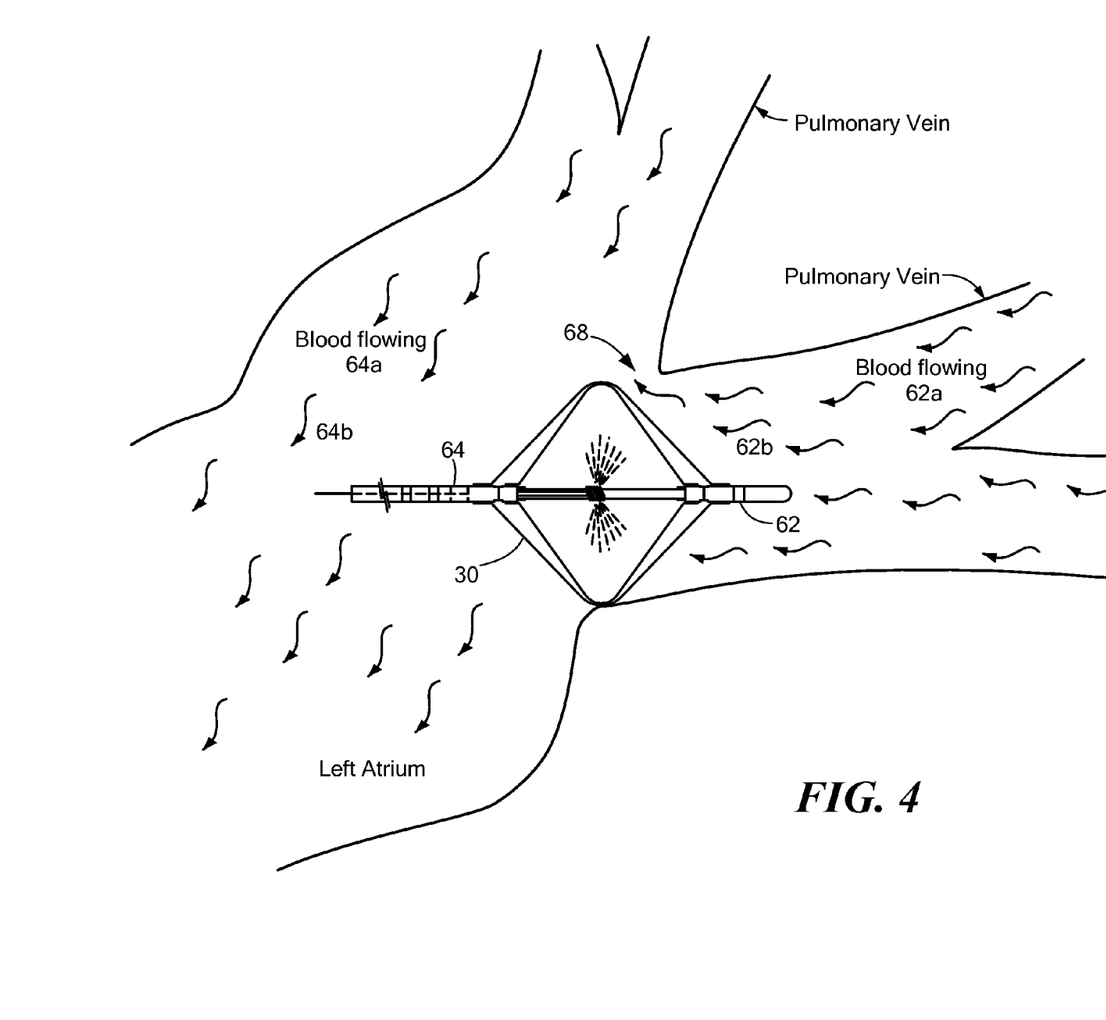
FIG. 4 is still another illustration of an example of a medical device achieving partial occlusion constructed in accordance with the principles of the present invention.

FIG. 4 illustrates catheter 12 as it would be used within the vascular system of a patient. The catheter 12 has the expandable element 30 radially expanded by inflation. As further shown in the embodiment, the catheter 12 is inserted through the vascular system to vessel 66. This configuration allows use of the catheter 12 by insertion through regions 62b and 64b, such as a cardiac chamber to abut vessel 66 exiting the chamber. The expandable element 30 is shown positioned near a desired site at vessel 66. In this orientation, however, expandable element 30 will not completely occlude or block the flow of blood from region 62b through vessel 66 because of the interruptions in the circumferential contact with the opening to the interior of vessel 66 at the target site. The expandable element 30 is not in contact with region 68, allowing blood 62a to flow towards region 64b.

When a complete occlusion is not achieved, both first temperature sensor 62 and second temperature sensor 64 are approximately the same temperature, as the blood flows through both of them. In an alternative embodiment, first temperature sensor 62 and second temperature sensor 64 may serve a dual function, i.e., as a sensor and an electrode. As such, first temperature sensor 62 and second temperature sensor 64 may be used for electrical mapping or may be used to provide information about tip location during navigation.

The determined temperature difference of the first temperature (measured at first temperature sensor 62) and the second temperature (measured at second temperature 64) may be correlated to a value that indicates whether there is a complete occlusion of vessel 66. The first temperature and the second temperature will have identical or substantially identical waveforms for a non-occluded vessel 66. In contrast, the first temperature and the second temperature will differ when the vessel 66 is occluded.

If the desired vessel 66 is occluded, the cold stagnant blood 62a, which has a known temperature—typically, about thirty-seven degrees Celsius—will create a decrease in the temperature measured by the first temperature sensor 62 and the temperature measured at first temperature sensor 62 will indicate that vessel 66 has not been occluded. As such, if there is no blood flow and the blood 62a is stationary (as in the case of an occluded vessel), there will be a constant temperature difference between the proximal second temperature sensor 64 and the distal first temperature sensor 62. The temperature of the distal first temperature sensor 62 will correspond generally to the temperature of the stationary blood, and the temperature of the proximal second temperature sensor 64 will correspond generally to the temperature of the flowing blood 64a.

On the other hand, if the vessel is not occluded, the first temperature sensor 62 and the second temperature sensor 64 will be in contact with the blood flowing past the expandable element 30, resulting in no or insignificant change in the temperature difference between the first temperature measured at the first temperature sensor 62 and the second temperature measured at the second temperature sensor 64. If blood flow is present across the two temperature sensors (as in the case of a partially or non-occluded vessel), the refrigerant will draw heat away from the blood and the temperature difference between the first temperature sensor 62 and second temperature sensor 64 will be small or the same. Several configurations and methods provide the ability to modify fluid delivery to achieve a constant flow. Accordingly, selective control of these configurations allows fluid flow to be regulated as desired.

In an exemplary embodiment, the refrigerant fluid may be pre-cooled before inflation. For instance, system 10 may be more efficient if the amount of the N2O refrigerant is pre-cooled by a sub-cooler at control unit 14. The pressure, density, velocity and the inherent characteristics of the fluid may be further modified in order to achieve a continuous fluid injection that will maintain a temperature differential and make occlusion assessment easier. Blood or other body fluids passing through the vicinity of the thermal device can reduce the quality of thermal exchange with the targeted tissue, which can then necessitate additional "cooling power" or refrigerant flow in the case of cryogenic treatments in order to complete the desired treatment.

In an alternative embodiment, the signal of the pressure measurement in region 62b and region 64b may be processed by processor 37 to provide a visual representation of a composite waveform that aggregates the signal waveforms of both region 62b and 64b. Alternatively, processor 37 may perform signal processing of the sensed signals to provide other parameters, including but not limited to text, numerical or graphical representations of the differential temperature.

It should be noted that although the first temperature sensor 62 and the second temperature sensor 64 have been disclosed, other forms of sensors may alternatively be used to measure other physiologic and hemodynamic parameters in either or both of region 62b and region 64b. For example, other sensors such as a pressure sensor, flow sensor, an optic sensor, a force sensor, or an electrical sensor or any other suitable sensor known in the art may be substituted.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system for occluding a blood vessel, comprising:
   an ablation catheter including:
      an elongate shaft with a proximal end, a distal end and a lumen disposed between the proximal end and the distal end;
      an expandable element in fluid communication with the lumen;
      a first temperature sensor operable to measure a first temperature;
      a second temperature sensor operable to measure a second temperature, the first temperature sensor and the second temperature sensor being longitudinally separated from each other by at least a portion of the expandable element; and
      a control unit operable to deliver a continuous flow of refrigerant to the expandable element and to determine a state of occlusion of the blood vessel based on a difference between the first temperature and the second temperature, the control unit including a processor that is programmed to deliver the continuous flow of refrigerant at a first flow rate during a positioning of the expandable element proximate an ostium of the blood vessel after the expandable element is inflated and to deliver the continuous flow of refrigerant at a second flow rate once the control unit determines the state of occlusion is that the blood vessel is occluded by the expandable element.

2. The medical system of claim 1, wherein the control unit is operable to:
   analyze a first temperature signal from the first temperature sensor;
   analyze a second temperature signal from the second temperature sensor; and
   derive a temperature differential between the first temperature sensor and the second temperature sensor based at least in part on the analysis of the first temperature signal and the second temperature signal.

3. The medical system of claim 1, wherein the extent of occlusion in the blood vessel is one of complete occlusion, partial occlusion and no occlusion, and wherein the control unit is further configured to:
   increase the continuous flow of refrigerant when it is determined that the extent of occlusion is complete occlusion.

4. The medical system of claim 1, wherein the control unit is further configured to:
   compare the determined temperature difference to a predetermined value of a plurality of predetermined values, wherein each predetermined value indicates the extent of occlusion in the blood vessel, and wherein the extent of occlusion is one of complete occlusion, partial occlusion and no occlusion; and
   determine the extent of occlusion in the blood vessel based at least in part on the comparison.

5. The medical system of claim 1, wherein the first flow rate is between approximately 1,000 and approximately 3,000 standard cubic centimeters per minute.

6. The medical system of claim 5, wherein the refrigerant is precooled prior to injection to a temperature in a range of approximately five degrees Celsius to ten degrees Celsius.

7. The medical system of claim 1, wherein the second flow rate is between approximately 6,200 and 7,200 standard cubic centimeters per minute.

8. The medical system of claim 1, wherein the first temperature sensor is positioned distal to the expandable element, and the second temperature sensor is positioned proximal to the expandable element.

9. A medical system, comprising:
   an ablation catheter including:
      an elongate shaft with a proximal end, a distal end and a lumen disposed between the proximal end and the distal end;
      an expandable element in fluid communication with the lumen;
      a first temperature sensor operable to measure a first temperature; and
      a second temperature sensor operable to measure a second temperature, the first temperature sensor and the second temperature sensor being longitudinally separated from each other by at least a portion of the expandable element; and
   a control unit operable to:
      deliver a continuous flow of refrigerant to the expandable element;
      determine an extent of occlusion by the expandable element in a blood vessel when the expandable element is inserted within the blood vessel and inflated, the determining being based at least in part on a temperature differential between the first temperature and the second temperature, the control unit being operable to deliver the continuous flow of refrigerant to the expandable element at between approximately 1,000 and approximately 3,000 standard cubic centimeters per minute during the determining and being operable to deliver the continuous flow of refrigerant to the expandable element at between approximately 6,200 and approximately 7,200 standard cubic centimeters per minute when the control unit determines the blood vessel is fully occluded.

* * * * *